US010392636B2

(12) United States Patent
Caulier

(10) Patent No.: US 10,392,636 B2
(45) Date of Patent: Aug. 27, 2019

(54) **METHOD FOR ENRICHING THE BIOMASS OF *THRAUSTOCHYTRIUM* GENUS MICROALGAE WITH DHA**

(71) Applicant: ROQUETTE FRERES, Lestrem (FR)

(72) Inventor: Bernard Caulier, Fretin (FR)

(73) Assignee: Roquette Freres, Lestrem (FR)

( * ) Notice: Subject to any disclaimer, the term of this patent is extended or adjusted under 35 U.S.C. 154(b) by 162 days.

(21) Appl. No.: 15/100,377

(22) PCT Filed: Dec. 18, 2014

(86) PCT No.: PCT/FR2014/053430
§ 371 (c)(1),
(2) Date: May 31, 2016

(87) PCT Pub. No.: WO2015/092301
PCT Pub. Date: Jun. 25, 2015

(65) Prior Publication Data
US 2016/0298149 A1    Oct. 13, 2016

(30) Foreign Application Priority Data
Dec. 19, 2013    (FR) ..................................... 13 62962

(51) Int. Cl.
*G01N 33/48* (2006.01)
*C12P 7/64* (2006.01)
*C12N 1/12* (2006.01)
*G06G 7/58* (2006.01)

(52) U.S. Cl.
CPC .............. *C12P 7/6472* (2013.01); *C12N 1/12* (2013.01)

(58) Field of Classification Search
None
See application file for complete search history.

(56) References Cited

U.S. PATENT DOCUMENTS
2009/0209014 A1    8/2009    Chi et al.

FOREIGN PATENT DOCUMENTS
WO    WO 01/54510    8/2001
WO    WO 2005/021735    3/2005

OTHER PUBLICATIONS

Chang, G. et al. "Fatty acid shifts and metabolic activity changes of *Schizochytrium* sp. S31 cultured on glycerol" *Bioresource Technology*, May 16, 2013, pp. 255-260, vol. 142.
Chang, G. et al. "The relationship of oxygen uptake rate and $k_La$ with rheological properties in high cell density cultivation of docosahexaenoic acid by *Schizochytrium* sp. S31" *Bioresource Technology*, Jan. 1, 2014, pp. 234-240, vol. 152.
Li, J. et al. "Comparative Metabolomics Analysis of Docosahexaenoic Acid Fermentation Processes by *Schizochytrium* sp. Under Different Oxygen Availability Conditions" *OMICS: A Journal of Integrative Biology*, May 2013, pp. 269-281, vol. 17, No. 5.
Qu, L. et al. "Batch, fed-batch and repeated fed-batch fermentation processes of the marine thraustochytrid *Schizochytrium* sp. for producing docosahexaenoic acid" *Bioprocess and Biosystems Engineering*, Dec. 15, 2013, pp. 1905-1912, vol. 36, No. 12.
Qu, L. et al. "Scale-up of docosahexaenoic acid production in fed-batch fermentation by *Schizochytrium* sp. based on volumetric oxygen-transfer coefficient" *Biochemical Engineering Journal*, May 15, 2013, pp. 82-87, vol. 77.
Zhang, L. et al. "Improving docosahexaenoic acid productivity of *Schizochytrium* sp. by a two-stage AEMR/shake mixed culture mode" *Bioresource Technology*, May 24, 2013, pp. 719-722, vol. 142.
Written Opinion in International Application No. PCT/FR2014/053430, dated Mar. 16, 2015, pp. 1-8.

*Primary Examiner* — Eric S Dejong

(57) ABSTRACT

The present invention relates to a fermenting method for enriching biomass of *Thraustochytrium* genus microalgae, specifically *Schizochytrium* sp. or *Schizochytrium mangrovei*, with docosahexaenoic acid (or DHA), by controlled addition of oxygen.

9 Claims, 1 Drawing Sheet

Specification includes a Sequence Listing.

METHOD FOR ENRICHING THE BIOMASS OF *THRAUSTOCHYTRIUM* GENUS MICROALGAE WITH DHA

CROSS-REFERENCE TO RELATED APPLICATION

This application is the U.S. national stage application of International Patent Application No. PCT/FR2014/053430, filed Dec. 18, 2014.

The present invention relates to a novel fermenting method for enriching a biomass of microalgae of the genus *Thraustochytrium*, more particularly *Schizochytrium* sp. or *Schizochytrium mangrovei*, in docosahexanoic acid (DHA), and also to the oil extracted from this microalgal biomass.

Lipids constitute one of the three major families of macronutrients with proteins and carbohydrates.

Among the lipids, triglycerides and phospholipids in particular stand out:

Triglycerides (also called triacylglycerols or triacylglycerides or TAGs) are glycerides in which the three hydroxyl groups of the glycerol are esterified with fatty acids. They are the main constituent of vegetable oil and of animal fats.

Triglycerides represent approximately 95% of the dietary lipids ingested by humans. In the organism, they are present mainly in adipose tissues and constitute the main form of energy storage.

Phospholipids are amphiphilic lipids, that is to say lipids consisting of a polar (hydrophilic) "head" and two aliphatic (hydrophobic) "tails".

Phospholipids are structural lipids since they are constituents of cell membranes for which they provide, inter alia, the fluidity.

Triglycerides and phospholipids are composed predominantly of fatty acids which are both provided by the diet and, for some of them, synthesized by the organism.

The biochemical classification (based on the number of double bonds contained in the fatty acid molecule) distinguishes saturated fatty acids (SFAs), monounsaturated fatty acids (MUFAs) and polyunsaturated fatty acids (PUFAs).

From the physiological point of view, the following are distinguished:

indispensible fatty acids, required for the development and correct functioning of the human body, but which our body is not able to produce;
"conditionally" indispensable fatty acids which are essential for normal growth and the physiological functions of cells, but which can be produced from their precursor if it is provided by the diet. They are therefore absolutely required if their essential precursor is absent;
non-indispensable fatty acids.

All the indispensable and "conditionally" indispensable fatty acids constitute essential fatty acids.

The other fatty acids are referred to as non-essential.

The non-indispensable fatty acids include, in particular:
eicosapentaenoic acid (EPA) of the omega 3 fatty acid family,
oleic acid, the predominant monounsaturated fatty acid in our diet, and palmitoleic acid,
saturated fatty acids, such as lauric acid, myristic acid or palmitic acid.

Polyunsaturated Fatty Acids

Polyunsaturated fatty acids are classified according to the position of the first double bond, starting from the final methyl function.

Thus, in the nomenclature, for omega "x" or "nx", "x" corresponds to the position of the first unsaturation.

Two major families of essential fatty acids are distinguished: omega 6 fatty acids (or n–6 PUFAs), of which the precursor and the major representative is linoleic acid (LA), and omega 3 fatty acids (or n–3 PUFAs), of which the precursor is alpha-linolenic acid (ALA).

The majority of the polyunsaturated fatty acids of biological interest belong to the omega 6 family (arachidonic acid or ARA) or omega 3 family (eicosapentaenoic acid or EPA, docosahexaenoic acid or DHA).

In addition, in the nomenclature, the number of carbons constituting the chain is also defined: thus, EPA is described as C20:5 and DHA as C22:6.

The "5" and "6" thus correspond to the number of unsaturations of the carbon chain presented respectively by EPA and by DHA.

DHA, of the omega 3 fatty acid family, is a fatty acid that the organism can synthesize from alpha-linolenic acid, or which is provided by the consumption of oily fish (tuna, salmon, herring, etc.).

DHA plays an important role in the structure of membranes and in the development and function of the brain and of the retina.

Fish oils are used mainly as a source of omega 3 fatty acids, such as DHA and EPA, but they are also found in oils of microalgae, from which they are extracted either as a mixture, or separately, as is the case for example with the oils derived from certain selected strains, such as those of the genus *Schizochytrium*, which contain only traces of EPA but high DHA contents.

Saturated Fatty Acids

Among the saturated fatty acids, palmitic acid, also referred to as hexadecanoic acid or cetyl acid, is one of the most common C16:0 saturated fatty acids in animals and plants.

Palmitic acid is the first fatty acid produced during lipogenesis; longer fatty acids can be produced from said palmitic acid.

Furthermore, it is the fatty acid preferentially used to synthesize ATP. The energy balance of the combustion thereof indicates 129 ATP. It thus constitutes an excellent energy food.

Industrially, palmitic acid is also used for the production of margarines and hard soaps.

In the paint field, given that it is saturated, palmitic acid cannot polymerize and become rigid once in contact with atmospheric oxygen (unlike oleic acid, linoleic acid and linolenic acid). It therefore remains in its soft solid form and acts (with stearic acid) as a plasticizer for polymerized oily binders. Thus, with stearic acid, it provides the elasticity required for good preservation of oil-containing pictorial materials over time.

Monounsaturated Fatty Acids

As monounsaturated fatty acid precursor, palmitic acid leads to palmitoleic acid (16:1, n–7), which is naturally present in large amounts in the fruit or pulp of sea buckthorn.

It has moreover been described that an increased provision of palmitoleic acid in food could have blood cholesterol-reducing and blood triglyceride-reducing effects, reduce the risk of stroke, and also improve metabolism in vascular smooth muscle cells.

Production of Lipids, Especially of Fatty Acids, by Microalgae

Microalgae of the genus *Schizochytrium* are conventionally cultured in fermenters (heterotrophic conditions: in darkness and in the presence of a carbon source).

It should be noted that the profitable utilization of these microalgae generally requires controlling the fermentation conditions.

To achieve this result, first methods for fermentation making it possible to obtain high cell densities (HCD) have thus been greatly developed in order to obtain maximum lipid yields and productivity.

The aim of these HCD cultures was to obtain the highest possible concentration of the desired lipids in the shortest period of time possible.

However, it quickly became apparent to specialists in the field that it is necessary for example to subject the microalgae to a nutritional stress which limits their growth, when it is desired to make them produce large lipid stores.

Therefore, growth and production are conventionally uncoupled in fermenting methods.

For example, to promote the accumulation of polyunsaturated fatty acids (in this instance docosahexanoic acid or DHA), patent application WO 01/54510 recommends dissociating cell growth from the production of polyunsaturated fatty acids.

More particularly, a method for producing microbial lipids is claimed, which method comprises the steps consisting in:

(a) carrying out fermentation of a medium comprising microorganisms, a carbon source and a limiting nutritional source, and ensuring conditions sufficient to maintain a dissolved oxygen content of at least approximately 4% of saturation in said fermentation medium to increase the biomass;

(b) then providing conditions sufficient to maintain a dissolved oxygen content of approximately less than or equal to 1% of saturation in said fermentation medium and providing conditions sufficient to allow said microorganisms to produce said lipids;

(c) and collecting said microbial lipids, in which at least 15% of said microbial lipids consist of polyunsaturated lipids;

and in which a biomass density of at least approximately 100 g/l is obtained over the course of the fermentation.

In the microalga *Schizochytrium* sp., strain ATCC 20888, a first growth phase is more particularly carried out in the presence of a carbon source and a nitrogen source but without limiting oxygen, so as to promote obtaining a high cell density, then, in a second phase, the supply of nitrogen is stopped and the supply of oxygen is gradually slowed (management of the dissolved oxygen pressure or $pO_2$ from 10% to 4% then to 0.5%), so as to stress the microalga, slow its growth and trigger production of the fatty acids of interest.

In the microalga *Crypthecodinium cohnii*, the higher DHA content is obtained at low glucose concentration (of the order of 5 g/l) and thus at a low growth rate (Jiang and Chen, 2000, Process Biochem., 35(10), 1205-1209).

Consequently, in the event that the formation of products is not correlated with high cell growth, it is taught that it is prudent to control the rate of cell growth.

In general, those skilled in the art choose to control the growth of the microalgae by controlling the fermentation conditions (temp, pH) or by regulated feeding of nutritional components to the fermentation medium (semi-continuous conditions referred to as "fed batch").

If they choose to control the growth of the microalgae in heterotrophy through the supply of carbon sources, those skilled in the art generally choose to adapt the carbon source (pure glucose, acetate, ethanol, etc.) to the microalga (*C. cohnii, Euglena gracilis*, etc.) as a function of the metabolite produced (for example a polyunsaturated fatty acid of DHA type).

Temperature may also be a key parameter. For example, it has been reported that the synthesis of polyunsaturated fatty acids in some species of microalgae, such as EPA by *Chiorella minutissima*, is promoted at a lower temperature than that required for the optimal growth of said microalga.

To optimize the production of triglycerides, those skilled in the art are also led to optimizing the carbon flow toward oil production, by acting on the nutritional environment of the fermentation medium.

Thus, it is known that oil accumulates when there is a sufficient supply of carbon but under conditions of nitrogen deficiency.

Therefore, the C/N ratio is a determining factor here, and it is accepted that the best results are obtained by acting directly on the nitrogen content, with the glucose content not being a limiting factor.

To optimize oil production, it is therefore essential for those skilled in the art to control the carbon flow by moving it toward oil production to the detriment of protein production; the carbon flow is redistributed and accumulates as lipid storage substances when the microalgae are placed in a nitrogen-deficient medium.

All of this aside, commercial preparations of microalgal biomass rich in DHA and palmitic acid are available by virtue of implementing standard fermentation conditions.

However, there is still an unfulfilled need for an alternative method for producing quality microalgal biomasses with a high DHA content and a controlled content of palmitic acid and/or palmitoleic acid.

SUMMARY OF THE INVENTION

The present invention relates to a method for producing a biomass of microalgae of the genus *Thraustochytrium* enriched in docosahexanoic acid (DHA), characterized in that, during the phase of culturing under heterotrophic conditions, the supply of oxygen is controlled so as to satisfy only the oxygen requirements 1) for energy production necessary for cell maintenance, 2) for base lipid production, and 3) for growth of the biomass apart from fatty acids.

Preferably, the method is characterized in that the supply of oxygen necessary to satisfy only the requirements 1), 2) and 3) is calculated by the following equation 2

$$qO2Target = \left(qm \times \frac{6 \times 32}{180}\right) + (q^{base\ lipids} \times y^{O2}/\text{lipids}) + (\mu \times y^{O2}/x)$$

in which $qO_2$Target is the amount of oxygen in grams per gram of biomass apart from fatty acids and per hour;

qm is the coefficient of maintenance expressed in g of glucose per g of biomass apart from fatty acids and per hour;

$q_{base\ lipids}$ is the rate of accumulation of base lipids expressed in g of base lipids per g of biomass apart from fatty acids and per hour;

$y^{O2}/_{lipids}$ is the coefficient of oxygen consumption relative to lipid formation expressed in g of oxygen per g of lipids;

μ is the rate of growth expressed in g of biomass formed apart from fatty acids per g of biomass apart from fatty acids and per hour, or ($h^{-1}$);

$y^{O2}/_x$ is the coefficient of oxygen consumption relative to biomass formation apart from fatty acids expressed in g of oxygen per g of biomass apart from fatty acids.

Optionally, no nutritional element, especially a carbon or nitrogen source, is limited during the fermenting method.

Optionally, the phases of growth and of DHA production are concomitant.

Preferably, the microalgae are of the genus *Schizochytrium* sp or *Schizochytrium mangrovei*. More specifically, the microalgae may be a strain selected from the strains CNCM I-4469 and CNCM I-4702 deposited with the Collection Nationale de Cultures de Microorganismes [French National Collection of Microorganism Cultures] of the Institut Pasteur on Apr. 14, 2011 and Nov. 22, 2012, respectively.

Optionally, the method may also comprise harvesting the biomass, optionally preparing a cell extract or lysate from this biomass, then optionally extracting a DHA-rich crude oil.

The method according to the present invention may be characterized in that the biomass obtained comprises:
  at least 40% of DHA by weight of total fatty acids; and/or
  at most 40% of palmitic acid by weight of total fatty acids; and/or
  at least 25% of fatty acids by dry weight of biomass.

DETAILED DESCRIPTION OF THE INVENTION

Figure 1:
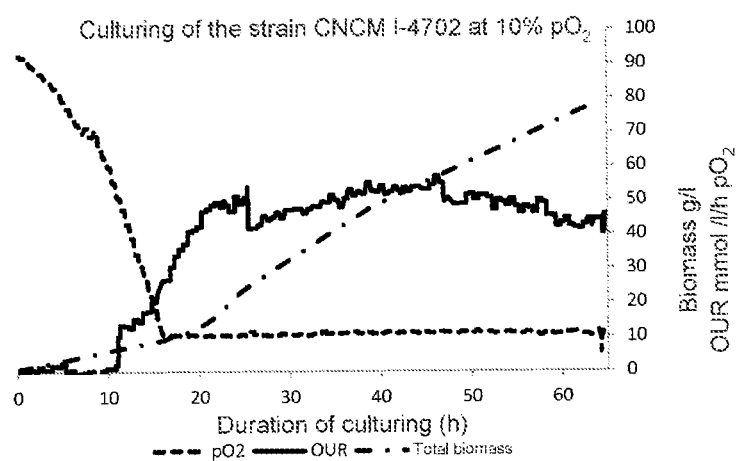
FIG. 1 shows culturing of the strain CNCM 1-4702 at 10% $pO_2$.

Within the context of the invention, the applicant company has chosen to explore an original route for optimizing the production of DHA by proposing an alternative solution to those conventionally envisioned by those skilled in the art.

The applicant company has thus found, going against the technical preconceptions in the art, that it is possible to produce by fermentation lipid-rich (more than 45% by dry weight of biomass) microalgal biomasses, the predominant fatty acids of which are docosahexanoic acid (DHA), while adjusting or controlling the amount of palmitic acid and palmitoleic acid:
  without it being necessary to uncouple the microalgal growth phase from the lipid production phase; on the contrary, lipid production is concomitant with cell growth and is therefore carried out in a single phase,
  without it being indispensable, as described in the prior art, to induce nitrogen limiting or limiting of any other nutritional element, and
  also without it being indispensable to control the fermentation through the $pO_2$.

The applicant company has thus found that it is possible to control the lipid composition of the biomass, and especially the proportions of DHA and of palmitic and palmitoleic acid by virtue of controlling the oxygenation of the fermentation medium.

Indeed, the applicant company has understood that oxygen is used by the microalgae according to the following priorities:
  energy production for maintenance,
  production of an array of fatty acids, referred to as base lipids, of which DHA is predominant,
  growth of the biomass apart from fatty acids, and
  production of palmitic acid with surplus oxygen.

In other words, the method in accordance with the invention consists in fulfilling the oxygen requirements corresponding to the first three points and thus providing the optimal amount of oxygen to obtain a DHA-rich biomass (whether it is produced by *Schizochytrium* sp or *S. mangrovei*).

Next, as will be demonstrated in the experimental section below, additional oxygen may be supplied and lead to rapid overproduction of palmitic acid (well illustrated with *S. mangrovei*), with or without palmitoleic acid (well illustrated with *Schizochytrium* sp).

The applicant company began its work based on the *Schizochytrium* sp strain ATCC 2088.

Following the teachings of the prior art, especially those of patent application WO 01/54510, the applicant company first of all found that, contrary to that which is disclosed, constant regulation of the $pO_2$ to 0% or to more than 10% for the entire duration of fermentation made it possible to produce more than 35% of PUFAs in the fatty acids (more than 25% DHA relative to total fatty acids), just as with managed operation with a cascaded reduction in $pO_2$ (10%, then 4%, then 0.5% of saturation).

On the other hand, the latter operation (according to application WO 01/54510) applied to strain CNCM I-4702 finally leads to production of fatty acids in which palmitic acid is highly predominant, at more than 60%, whereas DHA does not reach 20%; this operation gives the same results as those obtained for this strain with operation at constant $pO_2$ of 10%.

In addition, from a technical perspective, measuring $pO_2$ poses great problems when the protocol is scaled up from the laboratory to the industrial scale (in other words, scaling up from 1 to 20 l fermenters to 1 to 200 $m^3$ reactors).

Indeed, $pO_2$ is defined as the relative oxygen concentration dissolved in the fermentation must at saturation. For example, if water is aerated for long enough in air at room temperature and atmospheric pressure, it is considered that the $pO_2$ is equal to 100% (which corresponds to the state of oxygenation of the fermenter at t=0). In fact, when a $pO_2$ probe is calibrated in a fermenter, the dissolved oxygen content is influenced by the concentration of residual salts and by the fermentation temperature.

Moreover, it is conventionally accepted that, for a laboratory fermenter, the $pO_2$ is barely influenced by the pressure generated by the height of the fermentation must and by the mixing effects. However, during industrializations on fermenters of medium (of the order of 1 $m^3$) to large capacity (of the order of a few hundred $m^3$), the height of the fermentation must will, on the contrary:
  have an influence on the dissolved oxygen pressure; and
  cause complex phenomena in the "not perfectly stirred" fermenter.

In this sense, the $pO_2$ value established on the laboratory scale cannot therefore be extrapolated to the industrial scale.

Moreover, the recommendations of patent WO 01/54510 described for *Schizochytrium* sp do not appear to be generalizable to all strains of the genus *Thraustochytrium*. In other words, in the present invention, there is not a reduction in the oxygen supply so as to "stress" the microalga in order to make it produce its storage lipids (in this instance DHA), but rather there is a control of the oxygen supply to the extent of the requirements expressed by said microalga to adjust the direction of its lipid production, without referring to the $pO_2$.

Moreover, the choice to operate the fermentation by controlling the oxygen supply has led the applicant company to obtain remarkable results, without it being of any use to limit the supply of some nutritional substances, or to uncouple the growth phase from the production phase:
  increase in the overall content of lipids of interest, especially DHA, and odor reduction (the reduction in the particularly intense odor of the harvested biomasses of CNCM I-4469 is remarkable).

Choice of Microorganisms

The strains to be used in the methods of the present invention are of the genus *Thraustochytrium*, more particularly *Schizochytrium* sp or *Schizochytrium mangrovei*. Such strains are known to those skilled in the art. For example, mention may be made of the *Schizochytrium* sp strain ATCC No 20888, described and studied in application WO 01/54510.

In the course of their research, the applicant company has identified several microalgal strains of great interest which produce DHA. The applicant company is especially quite particularly interested in two strains that it has identified.

The first strain is a strain of *Schizochytrium* sp., deposited in France on Apr. 14, 2011 with the Collection Nationale de Cultures de Microorganismes [French National Collection of Microorganism Cultures] (CNCM) of the Institut Pasteur under number I-4469 and also in China with the CHINA CENTER FOR TYPE CULTURE COLLECTION (CCTCC) of the University of Wuhan, Wuhan 430072, P.R. China under number M 209118. This strain mainly produces DHA and to a lesser extent palmitic acid and palmitoleic acid. It was characterized by partial sequencing of the genes encoding 18 S RNA (SEQ ID No 1):

```
  1 GAGGGTTTTA CATTGCTCTC ATTCCAATAG CAAGACGCGA AGCGCCCCGC ATTGATATTT

61 CTCGTCACTA CCTCGTGGAG TCCACATTGG GTAATTTACG CGCCTGCTGC CTTCCTTGGA

121 TGTGGTAGCC GTCTCTCAGG CTCCCTCTCC GGAGTCGAGC CCTAACTCCC CGTCACCCGT

181 TATAGTCACC GTAGGCCAAT ACCCTACCGT CGACAACTGA TGGGGCAGAA ACTCAAACGA

241 TTCATCGCTC CGAAAAGCGA TCTGCTCAAT TATCATGACT CACCAAGAGA GTTGGCTTAG

301 ACCTAATAAG TGCGGCCCTC CCCGAAAGTC GGGCCCGTAC AGCACGTATT AATTCCAGAA

361 TTACTGCAGG TATCCGTATA AAGGAACTAC CGAAGGGATT ATAACTGATA TAATGAGCCG

421 TTCGCAGTTT CACAGTATAA TTCGCTTATA CTTACACATG CATGGCTTAG TCTTTGAGA
``` which made it possible to identify it as being a strain of *Schizochytrium* sp type. This strain will be subsequently denoted "CNCM I-4469" in the present application.

Moreover, the second strain is a strain of *Schizochytrium mangrovei*. It produces DHA and palmitic acid in relatively equal proportions. It was deposited by the applicant company in France on Nov. 22, 2012 with the Collection Nationale de Cultures de Microorganismes (CNCM) of the Institut Pasteur under number CNCM I-4702. It was characterized by sequencing of the genes encoding 18 S rRNA (SEQ ID No 2):

which made it possible to identify it as being a strain of *Schizochytrium mangrovei* type. This strain will be subsequently denoted "CNCM I-4702" in the present application.

Determining and Using the Necessary Amount of Oxygen, in Particular $qO_2$

The overall oxygen flow introduced into the culture medium is adjustable and depends essentially:
on the flow rate of the air introduced,
on the rate of stirring which promotes the dissolution of the oxygen in the medium.

This flow is referred to as OTR (Oxygen Transfer Rate).

The consumption of oxygen by the culture is referred to as OUR (Oxygen Uptake Rate).

When the biomass grows in the fermenter, its overall oxygen consumption increases until all the transferred oxygen is absorbed; the OUR is then considered to be equal to the OTR.

The OTR and the OUR are data for the whole of the culture medium. Thus, the OUR for a volume of culture may be relative to the amount of cells occupying this volume.

Thus, cellular consumption is referred to as $qO_2$ and represents the amount of $O_2$ in grams absorbed per gram of cell and per hour. This consumption is then calculated for the mass of cells as is, that is to say without the mass of the fatty acids, since the lipid stores do not have an active role in oxygen absorption.

By a controlled supply of oxygen to the culture medium, the method of the invention makes it possible to influence lipid production and to optimize it as a function of the microalgal growth conditions (inoculum size, culture age, etc.).

The overall $O_2$ consumption corresponds to the sum of the various uses of oxygen by the cell. The applicant company distinguishes four routes of oxygen consumption, which correspond to the fundamental requirements of the cell, which requirements are satisfied successively with an order of priority to the extent of the oxygen supply.

```
  1 GGTTTTACAT TGCTCTCATT CCGATAGCAA AACGCATACA CGCTTCGCAT CGATATTTCT

61 CGTCCTACCT CGTGGAGTCC ACAGTGGGTA ATTTACGCGC CTGCTGCTAT CCTTGGATAT

121 GGTAGCCGTC TCTCAGGCTC CCTCTCCGGA GTCGAGCCCT AACTCTCCGT CACCCGTTAT

181 AGTCACCGTA GTCCAATACA CTACCGTCGA CAACTGATGG GGCAGAAACT CAAACGATTC

241 ATCGACCAAA AWAGTCAATC TGCTCAATTA TCATGATTCA CCAATAAAAT CGGCTTCAAT

301 CTAATAAGTG CAGCCCCATA CAGGGCTCTT ACAGCATGTA TTATTTCCAG AATTACTGCA

361 GGTATCCATA TAAAAGAAAC TACCGAAGAA ATTATTACTG ATATAATGAG CCGTTCGCAG

421 TCTCACAGTA CAATCGCTTA TACTTACACA GCAG
```

These requirements, in order of priority, are the following:
1. Cell maintenance.
2. Base lipid production.
3. Formation of the biomass apart from fatty acids.
4. Lipid accumulation linked to metabolic excess.

The applicant company found that $qO_2$ is therefore determined by the following formula:

$$qO2 = \underbrace{\left(qm \times \frac{6 \times 32}{180}\right)}_{(1)} + \underbrace{(qbase \text{ lipids} \times y^{O2}/\text{lipids})}_{(2)} +$$

$$\underbrace{(\mu \times y^{O2}/x)}_{(3)} + \underbrace{(qexcess \text{ lipids} \times y^{O2}/\text{lipids})}_{(4)}$$

Equation (1)

The terms "qm", "$q_{base\ lipids}$", "$y^{O2}/_{lipids}$", "$\mu$", "$y^{O2}/_x$" and "$q_{excess\ lipids}$" of the equation should be understood as follows.

Cell Maintenance. Term (1) of the Equation

Cell maintenance corresponds to the energy required by the cell for its upkeep, independent of any lipid production or biomass growth.

"qm" is the amount of carbon-based substrate (generally glucose) used to produce this energy; it is expressed in g of glucose per g of biomass apart from fatty acids and per hour. This term is conventionally denoted in the field by "maintenance energy" or "maintenance coefficient".

The associated oxygen requirement is proportional. Indeed, 6 molecules of $O_2$ are needed (molar mass: 32 g) to convert one molecule of glucose (molar mass: 180 g), hence the term $$"qm \times \frac{6 \times 32}{180}"$$

in equation (1).

Base Lipid Production. Term (2) of the Equation

The applicant company has observed that lipid accumulation is concomitant with growth and is not just a phenomenon which appears when the latter stops. Lipid accumulation is a precursor to growth, albeit just for cell membrane formation.

The composition of these base lipids differs as a function of the strain and comprises, inter alia, palmitic acid or palmitoleic acid as DHA biosynthesis precursors, but DHA is always the predominant constituent, the quantification of which is illustrated by example 2.

The rate of accumulation of these lipids corresponds to a flow referred to as "$q_{base\ lipids}$" in equation (1).

For the *Schizochytrium* sp strain CNCM I-4469 and *Schizochytrium mangrovei* strain CNCM I-4702, this rate is illustrated by examples below.

To obtain the associated oxygen requirement, this flow or rate is multiplied by the oxygen requirement for lipid formation (also referred to as coefficient of oxygen consumption relative to lipid formation), expressed by the term "$y^{O2}/_{Lipids}$" in equation (1).

Thus, the oxygen supply will be used secondly for base lipid production.

Formation of the Biomass Apart from Fatty Acids. Term (3) of the Equation

The total biomass comprises the lipid stores.

The latter (consisting of fatty acids) are determined by assay and are subtracted from the total biomass.

Formation of the biomass apart from fatty acids (apart from "F.As") corresponds to the growth of the biomass which is rich in proteins and therefore genuinely active.

The growth rate is symbolized by "$\mu$" in equation (1), which represents the biomass (apart from F.As) in g formed per g of biomass (apart from F.As) and per hour, or ($h^{-1}$).

To obtain the associated oxygen requirement, this growth rate ($\mu$) is multiplied by the oxygen requirement for forming the biomass apart from F.As, expressed by the term: "$y^{O2}/_x$" in equation (1).

Thus, the oxygen supply is used thirdly for the production of biomass apart from fatty acids.

Calculating the Concentration of Biomass Apart from Fatty Acids

Growth is continuous since, in accordance with the method of the invention, there is no limiting of nutrition. However, slowing of the growth rate is observed, which is independent of the exhausting of the medium.

The concentration of biomass apart from F.As varies according to the initial biomass concentration and increases according to the growth rate thereof.

To predict the biomass concentration at each instant using calculation and to estimate the growth rate value, the applicant company recommends using the following equation (3).

$$\mu = \mu^{max}\left(1 - \frac{X}{X^{max}}\right) \qquad \text{Equation (3)}$$

This equation illustrates the observed and unexplained reduction in growth rate.

"$\mu$" represents the growth rate (expressed in $h^{-1}$) and X the cell concentration apart from F.As (expressed in g/l).

The parameters are different for the two preferred strains, and are reproduced in table I.

TABLE I

| Strain | Max $\mu$ | Max X (apart from F.As) |
|---|---|---|
| CNCM I-4469 | 0.08 $h^{-1}$ | 45 g/l |
| CNCM I-4702 | 0.17 $h^{-1}$ | 40 g/l |

This phenomenon also reduces $qO_2$, since the growth rate ($\mu$) contributes to oxygen consumption (equation 1).

The biomass concentration is calculated from the amount of biomass introduced and known (inoculum) and the rate of growth thereof which changes.

Accumulation of Lipids Linked to Metabolic Excess. Term (4) of the Equation

The applicant company has determined that the latter flow only exists once the abovementioned requirements have been satisfied and the necessary oxygen is supplied.

This oxygen supply, expressed in equation (1) by the term "$q_{excess\ lipids} \times y^{O2}/_{lipids}$" causes an increase in the rate of consumption of glucose, which will be converted into a fatty acid flow. This additional oxygen supply may be adjusted so as to control the production of the excess lipids.

This acceleration of fatty acid production, as illustrated in example 1, causes metabolic excess and leads to an accumulation of palmitic acid, for *Thraustochytrium*, and of palmitic acid and palmitoleic acid, for *Schizochytrium* sp. Without being bound by this theory, the applicant company considers that this excess is linked to the fact that the enzymes downstream in the metabolic pathway continue to work at the same rate, whereas the enzymes at the start of the metabolic pathway speed up their activity.

Calculation of $O_2$ Requirement to Form F.As and Biomass Apart from F.As

The $O_2$ conversion yields make it possible to know the $O_2$ consumptions as a function of the production of biomass apart from F.As or of lipids.

Conversion yields are parameters well known to those skilled in the art, who therefore may determine them by routine experiments.

These values are given in table II and are specific to the two preferred strains.

TABLE II

| | | |
|---|---|---|
| $O_2$ requirement for production of biomass apart from F.As (g/g) | 0.80 | $Y^{O2}/_x$ |
| $O_2$ requirement for lipid production (g/g) | 0.17 | $Y^{O2}/_{lipids}$ |

Obtaining a DHA-Rich Biomass—Calculating the Target $qO_2$

To increase the DHA content, the applicant company established that it was suitable to control the oxygen supply to only satisfy the first three oxygen uses (maintenance, base lipid production and growth of the biomass apart from F.As). This supply can be defined by determining the target $qO_2$, which corresponds to the amount of $O_2$ necessary in grams per gram of cells and per hour.

The target $qO_2$, is therefore defined by equation (2), which comprises only the first three components of equation (1).

$$qO2 Target = \underbrace{\left(qm \times \frac{6 \times 32}{180}\right)}_{(1)} + \underbrace{(qbase\ lipids \times y^{02}/lipids)}_{(2)} + \underbrace{(\mu \times y^{02}/x)}_{(3)} \quad \text{Equation 2}$$

Next, this rate of cellular consumption of $O_2$ is scaled up for the fermenter by multiplying it by the concentration of biomass apart from F.As, which may either be measured or predicted by calculation for each instant. This rate corresponds to the OUR.

Given that the conditions are such that OTR corresponds to OUR, it will therefore be this OTR which will be applied for each instant during the fermenting method.

The applicant company has found that by respecting this control of the target oxygenation, a DHA-rich biomass is obtained. Oxygenation greater than the target leads to the production of more palmitic acid and/or palmitoleic acid, and thus to the dilution of the DHA. Oxygenation less than the target oxygenation level limits the amount of biomass produced.

Since the target $qO_2$ varies with the evolution of the culture, reference is made in the following examples to the maximum OUR observed. Examples 1 and 2 illustrate the effect of controlling oxygenation on the *Schizochytrium* sp strain CNCM I-4469 and on the *Schizochytrium mangrovei* strain CNCM I-4702, and the method for obtaining specific production rates. Example 3 illustrates, for the *Schizochytrium mangrovei* strain CNCM I-4702, the effect of an operation in which the variation in oxygenation makes it possible to modify the proportions of palmitic acid and of DHA of the biomass.

In an alternative embodiment, the oxygen supply necessary to satisfy the first three requirements, namely requirements (1), (2) and (3), may also be determined empirically. As illustrated in example 3, those skilled in the art may carry out various fermenting methods in which a range of OTRs are used and the amounts of lipids and of biomass are measured. On the basis of these results, those skilled in the art may define the target OTR which makes it possible to satisfy the first three requirements.

The fermenting method according to the present invention makes it possible to obtain a biomass rich in fatty acids. Especially, the biomass comprises at least 25% of fatty acids by dry weight of biomass, preferably at least 30%. The fatty acid content may depend on the strain used and may reach a minimum of 40% by dry weight of biomass for the strain I-4702.

Moreover, and quite interestingly, this lipid-rich biomass has a high DHA content. Especially, the fermenting method according to the present invention makes it possible to obtain a biomass comprising at least 40% by weight of DHA relative to total fatty acids.

Finally, the fermenting method according to the present invention makes it possible to obtain a biomass having a reduced palmitic acid content. Thus, the biomass comprises at most 40% by weight of DHA relative to total fatty acids. The palmitic acid content may depend on the strain used and may reach a maximum of 10% by weight relative to total fatty acids for the strain I-4469.

Moreover, the present invention also considers fermenting methods in which the oxygen supply is greater than that necessary to satisfy the first three requirements, namely requirements (1), (2) and (3). Especially, this supply will be controlled so as to obtain the desired relative proportions of DHA and palmitic acid and/or palmitoleic acid, while optimizing the amount of biomass produced.

Moreover, the fermenting methods according to the present invention are carried out under heterotrophic culturing conditions. These conditions adapted to the microalgae under consideration and also the culture media are well known to those skilled in the art. The carbon source necessary for the growth of the microalga is preferably glucose. The nitrogen source may be extracts of yeast, urea, sodium glutamate, ammonium sulfate, aqueous ammonia with pH regulation, used separately or in combination. Generally, the culturing step comprises a preculturing step to revive the strain, then a step of culturing or fermentation proper. The latter step corresponds to the step of production of the lipids of interest, in particular of DHA.

Aside from the biomass, the present invention also relates to a cell extract or lysate prepared from this biomass. In particular, this extract or lysate is prepared from the biomass recovered after fermentation. This extract or lysate is rich in DHA and optionally in palmitic acid and/or palmitoleic acid. The cells may be ruptured to extract the lipid content by various routes, including mechanical, chemical and enzymatic routes.

Subsequently, an oil may be extracted from the cell lysate, for example by means of hexane/ethanol in several successive extractions. The hexane fraction is subsequently separated and then the hexane is evaporated to isolate the crude oil.

Thus, the method for producing lipids of interest, preferably DHA, and optionally palmitic acid and/or palmitoleic acid, comprises the fermenting method according to the present invention, harvesting the biomass, preparing a cell extract or lysate and extracting a crude oil comprising the lipids of interest, preferably DHA and optionally palmitic acid and/or palmitoleic acid.

EXAMPLES

Example 1: Conditions for Culturing Strains CNCM I-4469 and CNCM I-4702 and Determining the Specific Production Rates in Oxygenation Excess Culturing Conditions The protocol comprises preculturing in an Erlenmeyer flask for inoculation of the fermenter at 0.1 g of biomass/l for strain CNCM I-4469, and at least 5 g of biomass/l for strain CNCM I-4702.

Preculturing

Preculturing (100 ml of medium) in a 500 ml baffled Erlenmeyer flask lasts for 24 h at a temperature of 28° C.

All the components of the medium together are sterilized by filtration and introduced into an Erlenmeyer flask sterilized beforehand in an autoclave after addition of a drop of Clearol FBA 3107 antifoam.

TABLE III

| Preculture medium % (g/g) | |
|---|---|
| Anhydrous glucose | 3 |
| Yeast extract | 0.4 |
| Monosodium glutamate | 6.42 |
| NaCl | 1.25 |
| MgSO$_4$ 7(H$_2$O) | 0.4 |
| KCl | 0.05 |
| CaCl$_2$ 2(H$_2$O) | 0.01 |
| NaHCO$_3$ | 0.05 |
| KH$_2$PO$_4$ | 0.4 |
| Stock solution vitamins B1, B6, B12 | 0.1 |
| Stock solution trace elements | 0.8 |

Culturing

The medium is sterilized in 3 parts.

The glucose is sterilized with the KH$_2$PO$_4$ in an Erlenmeyer flask for an addition just before $T_0$.

The remainder of the salts are sterilized in the fermenter with 0.05 ml/l of Clearol FBA 3107. The trace elements and vitamins are sterilized by filtration.

The volume at $T_0$ represents 75% of the final volume. The pH is adjusted at $T_0$ using aqueous ammonia, then it is regulated at 6, still with aqueous ammonia.

TABLE IV

| Culture medium % (w/w) | |
|---|---|
| KH$_2$PO$_4$ | 0.80 |
| (NH$_4$)$_2$SO$_4$ | 0.33 |
| Na$_2$SO$_4$ | 0.67 |
| NaCl | 0.27 |
| CaCl$_2$ 2(H$_2$O) | 0.03 |
| MgSO$_4$7(H$_2$O) | 1.00 |
| Anhydrous glucose | 6.00 |
| Stock solution vitamins B1, B6, B12 | 0.20 |
| Stock solution trace elements | 0.27 |

A fed batch of glucose (concentration: 500 g/l of fed) is supplied continuously starting at $T_0$ at a constant rate (to be adapted according to calculations) so as not to be at a concentration lower than 20 g/l and 5 g/l at the end.

Culturing is carried out at a temperature of 28° C. for a duration of from 65 to 85 hours.

The use of corn steep liquor (CSL) or yeast extract (YE) as nitrogen source is possible, making it possible to obtain slightly higher DHA results.

Stock Solutions

TABLE V

| Trace elements | g/l |
|---|---|
| MnCl$_2$ 2H$_2$O | 8.60 |
| CoCl$_2$ 6H$_2$O | 0.2 |
| NiSO$_4$ 6H$_2$O | 7.50 |
| Na$_2$MoO$_4$ 2H$_2$O | 0.15 |
| ZnSO$_4$ 7H$_2$O | 5.70 |
| CuSO$_4$ 5H$_2$O | 6.50 |
| FeSO$_4$ 7 H$_2$O | 32.00 |
| Zinc acetate | 0.01 |
| EDTA | Brought to pH < 3 |

TABLE VI

| Vitamins | g/l |
|---|---|
| B1 | 45 |
| B6 | 45 |
| B12 | 0.25 |

Determining Specific Production Rates

To evaluate the specific production rates, a first culturing was carried out at a pO$_2$ of 10%, which means that there is always oxygen dissolved in the medium. This culturing was carried out without limiting nutritional sources.

This method makes it possible to demonstrate the characteristics of the strains to be tested, in oxygen excess (FIG. 1).

In table VII, the results given are those obtained at T65 of the culturing of the biomasses of the two strains CNCM I-4469 and CNCM I-4702.

TABLE VII

| Biomasses and fatty acid compositions | | |
|---|---|---|
| | CNCM I-4469 | CNCM I-4702 |
| Biomass (g/l) | 51.2 | 79 |
| F.A content/Total biomass (g/g) | 0.38 | 0.57 |
| DHA/F.A (g/g) | 0.34 | 0.19 |
| Palmitic acid/F.A (g/g) | 0.28 | 0.67 |
| Other fatty acids/F.A (g/g) | 0.38 | 0.14 |

F.A = fatty acid

The various fatty acids other than DHA and palmitic acids (especially palmitoleic acid) are subsumed under the title "other fatty acids" to demonstrate the effect on DHA and palmitic acid, but they are included in the base lipids along with DHA in the calculation of the target qO$_2$.

Calculation of the average rates is carried out globally.

The final biomass is analysed by gas chromatography (GC). The total biomass concentration, the content of each of the fatty acids and the overall content of fatty acids is then known.

The biomass apart from fatty acids, also referred to as active biomass, is calculated by deduction of these fatty acids from the total biomass.

The amount of each of the fatty acids produced is then divided by the average of the biomass apart from F.As present and by time. The result obtained is an overall specific production rate per unit time and per g of biomass apart from F.As.

These rates are given in table VII below.

TABLE VIII

Calculation of the rates

|  | CNCM I-4469 | CNCM I-4702 |
|---|---|---|
| µ active biomass (h$^{-1}$) | 0.05 | 0.055 |
| q Lipids (g/g/h) | 0.034 | 0.074 |
| q(DHA) (g/g/h) | 0.011 | 0.014 |
| q(palm) (g/g/h) | 0.009 | 0.050 |
| Q(other F.As) (g/g/h) | 0.013 | 0.010 |

Example 2: Culturing Strains CNCM I-4469 and CNCM I-4702 with a Controlled Oxygen Supply The same culturing conditions were used but the oxygen supply was controlled.

Figure 2:
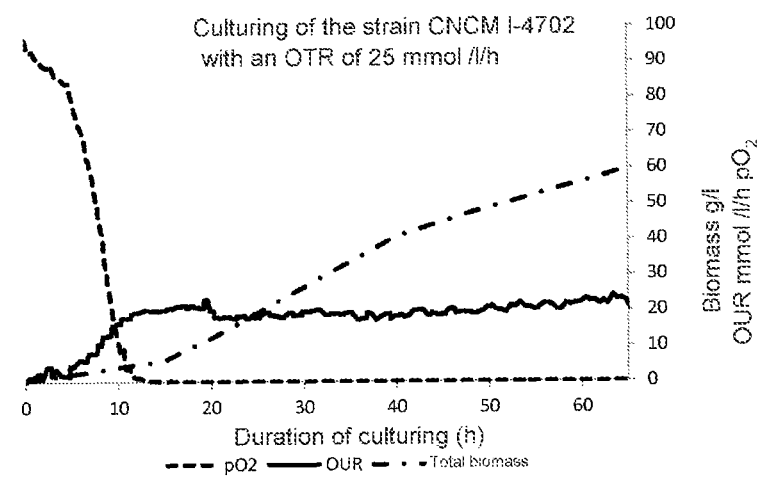
FIG. 2 shows culturing of the strain CNCM 1-4702 with an OTR of 25 mmol/l/h.

The method consists in using half the observed transfer value (OUR) during culturing at 10% (here: 50 mmol/l/h, cf. graph 1, i.e. 25 mml/l/h) (FIG. 2).

Moreover, for a 20 l fermenter, to respect the proper operation of the fermenter irrespective of the oxygenation requirements, a minimum stirring of the order of 150 rpm is fixed at $t_0$ for the first 10 to 15 hours of culturing.

In table IX, the results given are those obtained at T65 of the culturing of the biomasses of the two strains CNCM I-4469 and CNCM I-4702 under conditions of controlled $O_2$ supply.

TABLE IX

Biomasses and fatty acid compositions

|  | CNCM I-4469 | CNCM I-4702 |
|---|---|---|
| Biomass (g/l) | 34 | 59 |
| F.A content/Total biomass (g/g) | 0.29 | 0.45 |
| DHA/F.A (g/g) | 0.52 | 0.44 |
| Palmitic acid/F.A (g/g) | 0.04 | 0.39 |
| Other fatty acids/F.A (g/g) | 0.44 | 0.17 |

The average rates are calculated globally as indicated in example 1. The results are given in table X.

TABLE X

Calculation of the rates

|  | CNCM I-4469 | CNCM I-4702 |
|---|---|---|
| µ active biomass (h$^{-1}$) | 0.05 | 0.055 |
| q Lipids (g/g/h) | 0.021 | 0.045 |
| q(DHA) (g/g/h) | 0.011 | 0.02 |
| q(palm) (g/g/h) | 0.001 | 0.018 |
| Q(other F.As) (g/g/h) | 0.009 | 0.007 |

Comparing the global specific production rates in oxygen excess conditions (values from table VIII) and in controlled oxygen conditions, it is observed that:
- the oxygen supply has made it possible to reduce the rate of production of palmitic acid,
- the rate of production of palmitic acid has reduced by a factor of 9 for the strain CNCM I-4469 and by a factor of 3 for the strain CNCM I-4702.

This result is obtained even though the biomass or DHA production rates remain unchanged.

Thus, lipid production in the context of metabolic excess is prevented.

The rates evaluated by this method serve as a basis for the calculation of target $qO_2$.

Calculating $qO_2$ with Equations 1 and 2

The lipid production rates in table X represent here the constant flow of base lipids ($q_{base\ lipids}$ in equations 1 and 2), of which DHA is the predominant constituent, but which also contain a small amount of palmitic acid.

The flow for metabolic excess corresponds to the additional flow, between the rates from table VIII and those of table X.

qm is negligeable under non-stressing culturing conditions; a value of 0.006 g/g/h is retained.

The growth rate decreases with the increase in biomass concentration; the max. growth rate may be maintained at up to 4 g/l of biomass apart from lipids for CNCM I-4702 and 7 g/l for CNCM I-4469 inoculated at 5 g/l.

$qO_2$ (consumption at the cellular level) may be scaled up to OTR (corresponding to supply at the fermenter level) by taking into account the biomass concentration.

For the strain CNCM I-4469, at $\mu^{max}$ $$qO_{2Target}=0.006\times1.07+(0.011+0.001+0.009)\times0.17+0.08\times0.8=0.106\ g/g/h \quad \text{EQ 2:}$$

which corresponds to:

$OTR_{Target}=0.106\times7=0.74$ g of $O_2$ per l of culture and per hour or $OTR_{Target}=0.106\times7\times1000/32=23$ mmol of $O_2$/l of culture and per h For the strain CNCM I-4702, at $\mu^{max}$ $$qO_{2Target}=0.006\times1.07+(0.02+0.018+0.07)\times0.17+0.17\times0.8=0.218\ g/g/h \quad \text{EQ 2:}$$

which corresponds to:

$OTR_{Target}=0.218\times4=0.87$ (g of $O_2$ per l of culture and per hour)

$OTR_{Target}=0.218\times4\times1000/32=27.4$ mmol of $O_2$/l of culture and per h The use of these equations with the data from table X makes it possible to simulate culturing and determine the $OTR_{Target}$ to apply.

The latter decreases as the growth rate decreases, but this is partially compensated by the increase in the biomass concentration.

The $OTR_{Target}$ therefore remains close to that given above until the growth rate of the biomass apart from lipids reaches zero.

Example 3: Fermentation Operation with Different OTR Conditions

The tests carried out in examples 1 and 2, without limiting nutritional sources, make it possible to create a model by means of which it is possible to control lipid production by respecting a target $qO_2$ defined by equation 2 (which is equal to 27.4 mmol of $O_2$/l of culture and per h: cf. example 2).

From this initial target $qO_2$, variations were tested.

The degrees of variation, on either side of this target $qO_2$, are illustrated here by the max.OTR at the start of culturing.

The max.OTR value of between 25 and 30 corresponds to the optimum OUR at the start of culturing defined within the context of the invention for controlling the oxygen supply and in order to respect the target $qO_2$.

Table XI gives the fermentation parameters measured at T65 with CNCM I-4702.

TABLE XI

| % of target $qO_2$ | Max. OTR (mmol/l/h) at the start of culturing | Biomass (g/l) | Concentrations | | |
|---|---|---|---|---|---|
| | | | Fatty acids (g/100 g of biomass) | Palmitic acid (g/100 g of lipids) | DHA (g/100 g of lipids) |
| 60 | 15 | 41 | 41 | 36 | 48 |
| 75 | 20 | 52 | 41 | 36 | 46 |
| 100 | 25 | 57 | 47 | 39 | 45 |
| | 30 | 60 | 48 | 43 | 43 |
| 150 | 40 | 74 | 55 | 49 | 37 |
| 200 | 50 | 81 | 61 | 57 | 30 |

Thus, on the basis of these results, it may be observed that, when oxygen is supplied in excess relative to the value defined by equation 2, a dilution of the DHA in the excess lipids, especially palmitic acid, is observed.

On the contrary, when the oxygen supply is sub-optimal relative to the value defined by equation 2, the amount of DHA produced is smaller.

Example 4: Comparative Example with and without Limiting Nitrogen Deficiency

The tests were carried out with:
  as control: the strain CNCM I-4702, cultured under the conditions defined in the prior art consisting of patent application WO 01/54510, that is to say uncoupling of the growth phase and the production phase, the latter being induced during the step of limiting the nitrogen supply. This limiting was induced here by interrupting the pH regulation with aqueous ammonia at the end of the first third of the culturing.
  In order to only take account of the behavior of the strain CNCM I-4702 regarding its lipid production under nitrogen deficiency conditions, aeration was not regulated in a cascaded manner but rather maintained at a $pO_2$ of greater than 10%;
  fermentation in which, throughout the entire duration of culturing, the strain was not subjected to any nutritional limiting and the $pO_2$ was also regulated to 10%.

The results are as follows:

TABLE XII

| | No nutritional limiting | Nitrogen limiting |
|---|---|---|
| Biomass (g/l) | 76 | 86 |
| Fatty acids over biomass (g/g) | 0.57 | 0.65 |
| Palmitic acid/F.A (g/g) | 0.67 | 0.62 |
| DHA/F.A (g/g) | 0.21 | 0.24 |

The fatty acid-richness of the biomass is only very slightly decreased without nutritional limiting. Contrary to the technical preconceptions in the art, limiting a nitrogen source is therefore not necessary to induce lipid production.

Example 5: Comparative Example with the Strain ATCC 20888

The culturing protocol is that described in example 4 of patent application WO 01/54510. The strain used is *Schizochytrium* sp ATCC 20888.

The teaching of said application is followed, with comparison of the following two procedures:
  1. Permanent regulation greater than 10%.
  2. Constant $pO_2$ of 0%.

The results obtained are given in table XIII below.

TABLE XIII

| | Constant 0% $pO_2$ | $pO_2$ according to protocol WO 01/54510 (8 - 4 - 0.5 to 0%) | Constant 10% $pO_2$ |
|---|---|---|---|
| Time (h) | 74 | 74 | 74 |
| PUFAs/total fatty acids (%) | 44.0 | 43.8 | 36.1 |
| DHA/total fatty acids (%) | 33.6 | 32.8 | 27.1 |
| Total fatty acids (%) Biomass | 45.9 | 44.6 | 44.8 |
| Total biomass (g/l) | 166 | 147 | 187 |
| DHA g/l/h | 0.35 | 0.29 | 0.31 |
| DHA % Biomass | 15 | 15 | 12 |
| Inoculum (indicative) g/l | 23 | 10.5 | 11 |

By following the teachings of the prior art, especially those of patent application WO 01/54510, it is thus found that, contrary to that which is disclosed, constant regulation of the $pO_2$ to 0% or to more than 10% for the entire duration of fermentation made it possible to produce more than 35% of PUFAs in the fatty acids, just the same as with managed operation with a cascaded reduction in $pO_2$ (10%, then 4%, then 0.5% of saturation).

The invention claimed is:

1. A method for producing a biomass of microalgae of the genera *Thraustochytrium* and *Schizochytrium* enriched in docosahexanoic acid (DHA), comprising the steps of:
   (A) culturing microalgae of the genera *Thraustochytrium* and *Schizochytrium* under heterotrophic conditions,
   (B) determining the supply of oxygen according to the following equation:

$$qO2Target = \left(qm \times \frac{6 \times 32}{180}\right) + (qbase\ lipids \times y^{O2}/lipids) + (\mu \times y^{O2}/x)$$

in which
   $qO_2Target$ is the amount of oxygen in grams per gram of biomass apart from fatty acids and per hour;
   qm is the coefficient of maintenance expressed in g of glucose per g of biomass apart from fatty acids and per hour;
   $q_{base\ lipids}$ is the rate of accumulation of base lipids expressed in g of base lipids per g of biomass apart from fatty acids and per hour;
   $y^{O2}/_{lipids}$ is the coefficient of oxygen consumption relative to lipid formation expressed in g of oxygen per g of lipids;
   μ is the rate of growth expressed in g of biomass formed apart from fatty acids per g of biomass apart from fatty acids and per hours, or ($h^{-1}$);
   $y^{O2}/_x$ is the coefficient of oxygen consumption relative to biomass formation apart from fatty acids expressed in g of oxygen per g of biomass apart from fatty acids, and
   (C) controlling the supply of oxygen so as to satisfy only the oxygen requirements 1) for energy production necessary for cell maintenance, 2) for base lipid production, and 3) for growth of the biomass apart from fatty acids.

2. The method as claimed in claim 1, characterized in that no nutritional element is limited during the fermenting method.

3. The method as claimed in claim 1, characterized in that the phases of growth and of DHA production are concomitant.

4. The method as claimed in claim 1, characterized in that the microalgae are of the genus *Schizochytrium* sp. or *Schizochytrium mangrovei*.

5. The method as claimed in claim 1, characterized in that the microalgae are a strain selected from the strains CNCM I-4469 and CNCM I-4702 deposited with the Collection Nationale de Cultures de Microorganismes [French National Collection of Microorganism Cultures] of the Institut Pasteur on Apr. 14, 2011 and Nov. 22, 2012, respectively.

6. The method as claimed in claim 1, characterized in that it also comprises harvesting the biomass, optionally preparing a cell extract or lysate from this biomass, then optionally extracting a DHA-rich crude oil.

7. The method as claimed in claim 1, characterized in that the biomass obtained comprises at least 40% of DHA by weight of total fatty acids.

8. The method as claimed in claim 1, characterized in that the biomass obtained comprises, at most, 40% of palmitic acid by weight of total fatty acids.

9. The method as claimed in claim 1, characterized in that the biomass obtained comprises at least 25% of fatty acids by dry weight of biomass.

* * * * *

SEQUENCE LISTING

<160> NUMBER OF SEQ ID NOS: 2

<210> SEQ ID NO 1
<211> LENGTH: 479
<212> TYPE: DNA
<213> ORGANISM: Schizochytrium sp

<400> SEQUENCE: 1

```
gagggtttta cattgctctc attccaatag caagacgcga agcgccccgc attgatattt      60
ctcgtcacta cctcgtggag tccacattgg gtaatttacg cgcctgctgc cttccttgga    120
tgtggtagcc gtctctcagg ctccctctcc ggagtcgagc cctaactccc cgtcacccgt    180
tatagtcacc gtaggccaat accctaccgt cgacaactga tggggcagaa actcaaacga    240
ttcatcgctc cgaaaagcga tctgctcaat tatcatgact caccaagaga gttggcttag    300
```

-continued

```
acctaataag tgcggccctc cccgaaagtc gggcccgtac agcacgtatt aattccagaa        360
ttactgcagg tatccgtata aaggaactac cgaagggatt ataactgata taatgagccg        420
ttcgcagttt cacagtataa ttcgcttata cttacacatg catggcttag tctttgaga         479

<210> SEQ ID NO 2
<211> LENGTH: 454
<212> TYPE: DNA
<213> ORGANISM: Schizochytrium mangrovei

<400> SEQUENCE: 2
ggttttacat tgctctcatt ccgatagcaa aacgcataca cgcttcgcat cgatatttct         60
cgtcctacct cgtggagtcc acagtgggta atttacgcgc ctgctgctat ccttggatat        120
ggtagccgtc tctcaggctc cctctccgga gtcgagccct aactctccgt cacccgttat        180
agtcaccgta gtccaataca ctaccgtcga caactgatgg ggcagaaact caaacgattc        240
atcgaccaaa awagtcaatc tgctcaatta tcatgattca ccaataaaat cggcttcaat        300
ctaataagtg cagccccata cagggctctt acagcatgta ttatttccag aattactgca        360
ggtatccata taaaagaaac taccgaagaa attattactg atataatgag ccgttcgcag        420
tctcacagta caatcgctta tacttacaca gcag                                    454
```